United States Patent [19]

Lösel et al.

[11] 4,322,418

[45] Mar. 30, 1982

[54] SUBSTITUTED 1-(α-AMINOCARBONYL-BENZYL)-3,4-DIHYDRO-ISOQUINOLINES, COMPOSITIONS AND USE

[75] Inventors: Walter Lösel, Gau-Algesheim; Franz Esser, Ingelheim am Rhein; Otto Roos, Schwabenheim; Richard Reichl, Gau-Algesheim; Franz J. Kuhn, Bingen; Werner Traunecker, Münster-Sarmsheim, all of Fed. Rep. of Germany

[73] Assignee: C. H. Boehringer Sohn, Ingelheim am Rhein, Fed. Rep. of Germany

[21] Appl. No.: 250,667

[22] Filed: Apr. 3, 1981

[30] Foreign Application Priority Data

Apr. 11, 1980 [DE] Fed. Rep. of Germany ....... 3013906

[51] Int. Cl.³ .................. A61K 31/535; A61K 31/47; C07D 413/06; C07D 217/18

[52] U.S. Cl. .......................... 424/248.57; 424/248.58; 424/250; 424/258; 544/126; 544/128; 544/361; 544/363; 546/90; 546/146

[58] Field of Search ............... 544/126, 361, 363, 128; 546/90, 146; 424/248.57, 248.58, 250, 258

[56] References Cited

U.S. PATENT DOCUMENTS 2,769,810 11/1956 Ochiai et al. .................... 546/146
3,207,759 9/1965 Creighton et al. ................ 546/146

*Primary Examiner*—Henry R. Jiles
*Assistant Examiner*—R. W. Ramsuer
*Attorney, Agent, or Firm*—Hammond & Littell, Weissenberger and Muserlian

[57] ABSTRACT

This invention relates to substituted 1-(α-aminocarbonyl-benzyl)-3,4-dihydro-isoquinolines in the racemic or optically active form and the non-toxic pharmacologically acceptable salts thereof. These compounds are useful in the promotion of blood circulation in warm-blooded animals.

7 Claims, No Drawings

SUBSTITUTED 1-(α-AMINOCARBONYL-BENZYL)-3,4-DIHYDRO-ISOQUINOLINES, COMPOSITIONS AND USE

FIELD OF THE INVENTION

This invention relates to novel substituted 1-(α-aminocarbonyl-benzyl)-3,4-dihydro-isoquinolines and non-toxic acid addition salts thereof, to methods of preparing these compounds, to pharmaceutical compositions containing them as active ingredient, and to methods of using them as blood circulation promoting agents.

More particularly, the present invention relates to a novel class of compounds represented by the formula

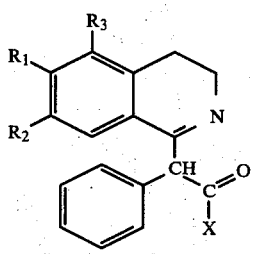 (I)

wherein $R_1$, $R_2$, $R_3$, which may be the same or different, each represent a hydrogen, hydroxyl, or methoxy group or $R_1$ and $R_2$, $R_2$ and $R_3$, or $R_1$ and $R_3$ together represent a methylenedioxy group; and X represents a dialkylamino in which each alkyl moiety has from 1 to 3 carbon atoms; a heterocyclic group such as an aziridinyl, azetidinyl, pyrrolidinyl, morpholino, N'-methylpiperazino, or N'-benzylpiperazino group; or the group

—NHR wherein R represents a lower alkyl group of from 1 to 4 carbon atoms; alkenyl or alkinyl group of 3 carbon atoms; cycloalkyl group of from 3 to 6 carbon atoms; morpholino group; pyridyl group; or ethyl or propyl group substituted by a hydroxyl, methoxy, dimethylamino, phenyl, methoxyphenyl, dimethoxyphenyl, methylenedioxyphenyl, morpholino, or indolyl group, in racemic or optically active form, and non-toxic, pharmacologically acceptable acid addition salts thereof.

The acid addition salts comprise any desired pharmacologically acceptable salts formed with inorganic or organic acids. Examples of suitable such salts include hydrohalides such as hydrochlorides, sulfates, hydrogen sulfates, phosphates, hydrogen phosphates, tartrates, succinates, maleates, benzoates, acetates, propionates, lactates, ascorbinates, and the like.

The compounds according to the invention may be prepared by cyclizing a (mixed) diamide of phenylmalonic acid of the formula

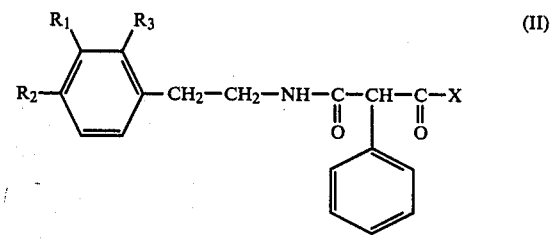 (II)

wherein $R_1$, $R_2$, $R_3$, and X are as defined above, in the presence of a suitable condensing agent, in a manner known per se, to form the corresponding 3,4-dihydroisoquinoline. Subsequently, if desired, a salt obtained is converted into the free base and/or the free base obtained is converted with a pharmacologically acceptable acid into the salt thereof.

Examples of suitable condensing agents include numerous Lewis acids, such as, for example, phosphorus oxychloride, boron trifluoride, stannic tetrachloride, or titanium tetrachloride, as well as strong inorganic acids such as sulfuric acid, fluorosulfonic acids, hydrofluoric acid, or polyphosphoric acid. The condensing agents are normally used in excess. Phosphorus oxychloride is preferred.

The cyclization reaction may be carried out with or without a solvent. All inert solvents are suitable, provided that they are sufficiently soluble for the reaction partners and have a sufficiently high boiling point. Examples include benzene, alkylbenzenes, chlorobenzenes, decalin, chloroform, methylene chloride, acetonitrile, and the like. In an alternative embodiment of the process, the condensing agent itself, for example, phosphorus oxychloride, is used as the solvent.

No special conditions apply with regard to the reaction temperature. The reaction according to the invention may be effected within a wide temperature range, preferably with heating up to approximately the boiling point of the solvent.

The starting compounds of Formula II, some of which are new, may be prepared, for example, according to the following reaction scheme:

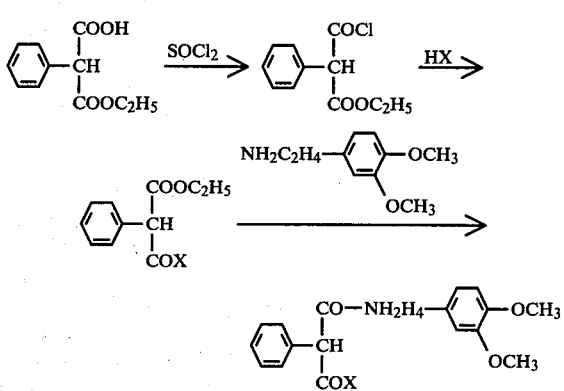

In the initial stage, phenylmalonic acid is treated with thionyl chloride and further reacted with an amine of the formula HX, wherein X is as defined above. The compound of Formula II is then obtained by reaction with 2-(3',4'-dimethoxyphenyl)-ethylamine in a nitrogen atmosphere.

The compounds according to the invention are used as agents in promoting blood circulation, that is, they improve the passage of blood through the tissues and the supply of oxygen to tissues, particularly in the central nervous system. They also have the effect of increasing contractility and influencing blood pressure. Compounds wherein X is a cyclized heterocyclic system or a dialkylamine are particularly effective.

The compounds of Formula I in racemic or optically active form and the acid addition salts thereof may also be used in conjunction with active substances of other kinds. Suitable galenic forms for administration include, for example, tablets, capsules, suppositories, solutions, or powders. For their preparation, the conventional galenic excipients, carriers, disintegrants, or lubricants or substances for obtaining sustained release may be used.

The compounds according to the invention have a significantly longer-lasting activity than standard commercial products. In comparison with xanthinol nicotinate, they have a 60% superiority, based on the increased flow of blood through the brain in a cat.

The inhibition of thiopental-induced damage to a rat's paw shows a dosage ratio of 1:100 with the above-mentioned comparison substance for the blood flow-promoting and circulation-stimulating effect. For the resorption coefficient, i.e., the ratio of oral to intravenous dosage, the compounds according to the invention have a superiority of 2:1. A dosage range of from about 1 to 50 mg/kg, preferably from about 10 to 40 mg/kg, per os, or from about 0.1 to 10 mg/kg, preferably from about 2 to 7 mg/kg, intravenously, is recommended.

The following examples are intended to illustrate the invention and should not be construed as limiting the invention thereto.

EXAMPLES

The following examples are representative preparations of compounds of Formula II:

EXAMPLE 1

Monoethyl phenylmalonate chloride

One hundred five grams (0.5 mol) of monoethyl phenylmalonate [JACS 74, 5897 (1952)] were refluxed with 119 gm of thionyl chloride in a water bath for 90 minutes, under stirring. The excess thionyl chloride was eliminated in vacuo, and the residue was distilled under reduced pressure (130° to 135° C./15 mm). An amount of 85.0 gm (75% of theory) of monoethyl phenylmalonate chloride was obtained.

EXAMPLE 2

Monoethyl phenylmalonate-2-(3',4'-dimethoxyphenyl)-ethylamide

Two hundred ninety-five grams (1.3 mol) of monoethyl phenylmalonate chloride in 500 ml of absolute tetrahydrofuran were added dropwise, at room temperature, to a cooled mixture of 236 gm (1.3 mol) of 2-(3',4'-dimethoxyphenyl)-ethylamine, 171 gm of triethylamine, and 500 ml of absolute tetrahydrofuran, under stirring and in a protective $N_2$ atmosphere. After the reaction ended, the precipitated triethylammonium chloride was suction filtered, the filtrate was concentrated, and the solid residue was distributed between water and methylene chloride. The organic phase was dried over $Na_2SO_4$. After the solvent evaporated, the product was recrystallized from ethyl acetate.

M.p.: 103° C., yield: 342 gm (71% of theory).

EXAMPLE 3

α-Diethylaminocarbonyl-phenylacetic acid-2-(3',4'-dimethoxyphenyl-ethylamide

A mixture of 16.7 gm of monoethyl phenylmalonate-2-(3',4'-dimethoxyphenyl)-ethylamide and 120 ml of diethylamine was heated to 120° to 130° C. in an autoclave for 48 hours. The reaction mixture was then mixed with 500 ml of ethanol and treated with active charcoal at boiling temperature. After cooling, the reaction mixture was suction filtered and then concentrated by evaporation, and the residue was crystallized from ethyl acetate/petroleum ether at 40° to 80° C., after purification on a silica gel column ($CH_2Cl_2$/MeOH ratio of 100:1 to 100:2).

M.p.: 81°–85° C.; yield: 14 gm (78% of theory).

The following examples are representative preparations of compounds of Formula I:

EXAMPLE 4

1-(α-Diethylaminocarbonyl-benzyl)-6,7-dimethoxy-3,4-dihydroisoquinoline hydrochloride Thirty-three grams of α-diethylaminocarbonyl-phenylacetic acid-2-(3',4'-dimethoxyphenyl)-ethylamide were dissolved in 120 ml of acetonitrile and mixed with 18 ml of phosphorus oxychloride. The reaction mixture was refluxed for about 2 hours. It was then concentrated by evaporation, and the residue was taken up in 200 ml of methylene chloride and rendered alkaline by stirring into a solution of potassium carbonate in ice water. After processing in the usual way (extracting with methylene chloride, drying the organic phase over $Na_2SO_4$, eliminating the solvent, etc.), the product was purified over a silica gel column ($CH_2Cl_2$/MeOH ratio of 100:1 to 100:2).

M.P.: 170° C.; yield: 26 gm.

To obtain the hydrochloride, 26 gm of base were dissolved in as small an amount of ethanol as possible and mixed with ethanolic hydrochloric acid. The hydrochloride was crystallized out by dropwise addition of absolute ether and petroleum ether (1:1) at 40° to 80° C.

M.p.: 203°–205° C.; yield: 17 gm (49.2% of theory).

EXAMPLE 5

1-(α-Dimethylaminocarbonyl-benzyl)-6-methoxy-3,4-dihydroisoquinoline-hydrochloride An amount of 3.9 gm (11.5 mmol) of phenylmalonic acid dimethylamide-[2-(3-methoxyphenyl)-ethylamide] was dissolved in 60 ml of chloroform, and the resulting solution was then mixed with 13.7 gm (90 mmol) of $POCl_3$ and refluxed for 6 hours. The solvent was removed in a rotary vaporizer, the residue was dissolved in $CH_2Cl_2$, and that solution was added dropwise to a cold saturated $K_2CO_3$ solution. After extraction three times with $CH_2Cl_2$, the combined organic extracts were extracted three times with 2 N HCl. The combined HCl phases were made alkaline with $K_2CO_3$ and again extracted with $CH_2Cl_2$. The organic phase was dried and then concentrated under reduced pressure, and the residue was treated with ethereal HCl. The hydrochloride precipitated was dissolved in isopropanol, the solution was treated with active charcoal, and diethyl ether was added to the solution until the solution began to become turbid. After being left overnight in a refrigerator, the desired compound crystallized out as the hydrochloride.

Yield: 2.3 gm (56% of theory). M.p.: 124° C.

The compounds set forth in the following table were prepared using analogous procedures:

TABLE 1

$R_1 = R_2 = $ methoxy, $R_3 = $ hydrogen

| Example No. | X | Salt form | M.p. (°C.) |
|---|---|---|---|
| 6 | —NHCH$_3$ | Hydrochloride | 220° |
| 7 | —N(CH$_3$)$_2$ | Hydrochloride | 153–155° |
| 8 | —NHC$_2$H$_5$ | Base | 155–157° |
| 9 | —N(C$_2$H$_5$)$_2$ | Hydrochloride | 190° |
| 10 | —NH—CH$_2$—CH$_2$—OH | Hydrochloride | 212° |
| 11 | —NH—CH$_2$—CH$_2$—OCH$_3$ | Base | 107° |
| 12 | —NH—CH$_2$—CH$_2$—CH$_2$—OCH$_3$ | Hydrochloride | 164° |
| 13 | —NH—CH$_2$—CH(CH$_3$)$_2$ | Hydrochloride | 214° |
| 14 | —NH—CH$_2$—CH$_2$CH$_2$—N(CH$_3$)$_2$ | Dihydrochloride | 224–226° |
| 15 |  | Hydrochloride | 157–159° |
| 16 | 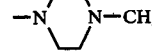 | Base | 78–80° |
| 17 | 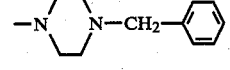 | Dihydrochloride | 226–229° |
| 18 | 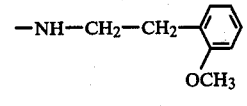 | Base | 140° |
| 19 | 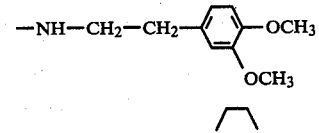 | Hydrochloride | 161° |
| 20 | 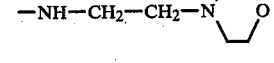 | Base | 152° |
| 21 | 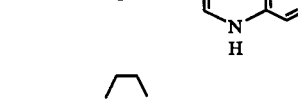 | Base | 163° |
| 22 | 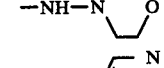 | Base | 193–195° |
| 23 | 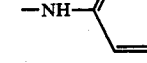 | Hydrochloride | 197–202° |
| 24 | 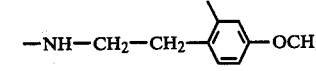 | Base | 168–170° |
| 25 | 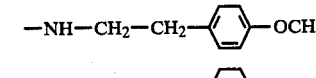 | Base | 123–125° |
| 26 | 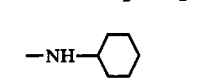 | Hydrochloride | 109° |
| 27 | 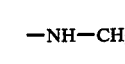 | Base | 130–135° |
| 28 | 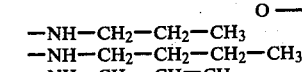 | Base | 118–120° |
| 29 | —NH—CH$_2$—CH$_2$—CH$_3$ | Hydrochloride | 71–78° |
| 30 | —NH—CH$_2$—CH$_2$—CH$_2$—CH$_3$ | Hydrochloride | 79–81° |
| 31 | —NH—CH$_2$—CH=CH$_2$ | Hydrochloride | 205–207° |
| 32 | —NH—CH$_2$—C≡CH | Hydrochloride | 173–175° |
| 33 | —NH—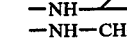 | Hydrochloride | 227–228° |
| 34 | —NH—CH(CH$_3$)$_2$ | Hydrochloride | 226–227° |
| 35 | —NH—C(CH$_3$)$_3$ | Hydrochloride | 225–226° |

TABLE 1-continued $R_1 = R_2 = $ methoxy, $R_3 = $ hydrogen

| Example No. | X | Salt form | M.p. (°C.) |
|---|---|---|---|
| 36 | —NH—CH₂—CH₂—CH₂—CH₂—CH₃ | Hydrochloride | 88–94° |
| 37 | —NH—CH(CH₃)—CH₂—CH₃ | Hydrochloride | 214–215° |
| 38 | —NH—CH₂—CH₂—CH(CH₃)₂ | Hydrochloride | 90–93° |
| 39 | —NH—CH₂—CH(OH)—CH₃ | Hydrochloride | 201–202° |
| 40 | —NH—CH₂—CH₂—N(CH₃)₂ | Dihydrochloride | 134–143° |
| 41 | 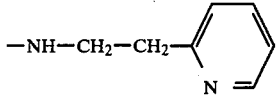 | Base | 110–112° |
| 42 | 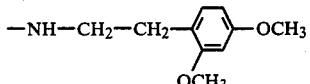 | Base | 168–170° |
| 43 | 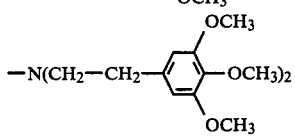 | Hydrochloride | 54–64° amorphous |
| 44 |  | Hydrochloride | 59–68° amorphous |
| 45 |  | Hydrochloride | 195–197° |
| 46 | 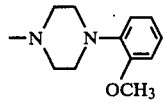 | Hydrochloride | 183° |
| 47 | 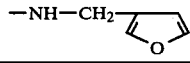 | Base | 80–83° |

TABLE 2

$R_1, R_2 = $ Methylenedioxy, $R_3 = $ Hydrogen

| Ex. No. | X | Salt form | M.p. (°C.) |
|---|---|---|---|
| 48 | 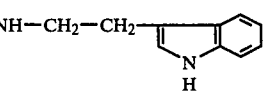 | Base | 99–90° |
| 49 | 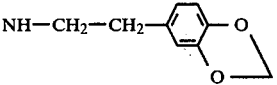 | Hydrochloride | 115–120° |
| 50 | 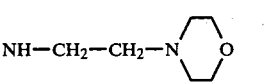 | Base | 155–156° |
| 51 |  | Base | 165° |
| 52 |  | Base | 199° |

TABLE 3

$R_1 = $ Methoxy, $R_2 = $ Hydroxyl, $R_3 = $ Hydrogen

| Ex. No. | X | Salt form | M.p. (°C.) |
|---|---|---|---|
| 53 | 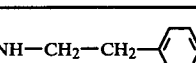 | Hydrochloride | 108–112° |
| 54 | —NH—CH₂—CH(CH₃)₂ | Base | 154– |
| 55 | 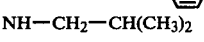 | Hydrochloride | 158° 158–163° |
| 56 |  | Base | 143–146° |
| 57 | 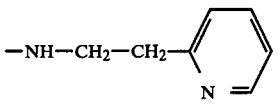 | Base | 216–218° |
| 58 | 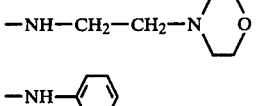 | Base | 148–153° |
| 59 | 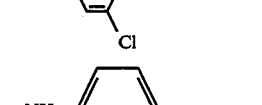 | Hydrochloride | 177–183° |
| 60 | 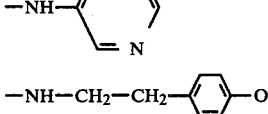 | Hydrochloride | 136° |

TABLE 3-continued $R_1$ = Methoxy, $R_2$ = Hydroxyl, $R_3$ = Hydrogen

| Ex. No. | X | Salt form | M.p. (°C.) |
|---|---|---|---|
| 61 | —NH—CH$_2$—CH$_2$—C$_6$H$_3$(OCH$_3$)(OCH$_3$) | Hydrochloride | 161–165° |
| 62 | —N(piperazinyl)—C$_6$H$_4$—OCH$_3$ | Hydrochloride | 198° |
| 63 | —NH—C$_6$H$_3$(CH$_3$)(Cl) | Hydrochloride | 167° |
| 64 | —N(CH$_2$C$_6$H$_5$)(CH$_2$—CH$_2$—CN) | Hydrochloride | 167–172° |
| 65 | —NH—CH$_2$—CH$_2$—CH$_2$—CH$_2$—CH$_3$ | Base | 149° |
| 66 | —NH—CH$_2$—CH$_2$—CH$_2$—CH$_3$ | Base | 147° |
| 67 | —NH—CH$_2$—CH=CH$_2$ | Base | 167–169° |
| 68 | —NH—CH(CH$_3$)$_2$ | Hydrochloride | 152° |
| 69 | —NH—(2-pyridyl) | Base | 129–131° |

TABLE 4

$R_1$ = Hydroxy, $R_2$ = Methoxy, $R_3$ = Hydrogen

| Example No. | X | Salt form | M.p. (°C.) |
|---|---|---|---|
| 70 | —N(C$_2$H$_5$)$_2$ | Hydrochloride | 199° |

TABLE 5

$R_1$ = Methoxy, $R_2$ = $R_3$ = Hydrogen

| Ex. No. | X | Salt form | M.p. (°C.) |
|---|---|---|---|
| 71 | —NH—C$_2$H$_5$ | Hydrochloride | 158° |
| 72 | —NH—CH$_3$ | Hydrochloride | 155° |
| 73 | —NH—CH$_2$—CH$_2$—C$_6$H$_4$—OCH$_3$ | Hydrochloride | 104° (decomp.) |
| 74 | —N(CH$_3$)C$_2$H$_5$ | Hydrochloride | ~60° hygroscopic |
| 75 | —NH—CH$_2$—C$_6$H$_5$ | Hydrochloride | ~120° |

TABLE 6

$R_1$ = $R_2$ = $R_3$ = Methoxy

| Ex. No. | X | Salt form | M.p. (°C.) |
|---|---|---|---|
| 76 | —N(CH$_3$)C$_2$H$_5$ | Toluenesulfonate | hygroscopic |
| 77 | —NH—CH$_2$—C$_6$H$_5$ | Hydrochloride | 180° |
| 78 | —NH—CH$_2$—CH$_2$—C$_6$H$_2$(OCH$_3$)(OCH$_3$)(OCH$_3$) | Hydrochloride | 89° (decomp.) |
| 79 | —NH—(4-pyridyl) | Base | 117–120° |

The following examples illustrate a few pharmaceutical dosage unit compositions comprising a compound of the present invention as an active ingredient.

EXAMPLE 80

Tablets
Composition of one tablet:

| Component | Amount |
|---|---|
| Active ingredient according to the invention | 40.0 mg |
| Lactose | 100.0 mg |
| Corn starch | 50.0 mg |
| Colloidal silicic acid | 2.0 mg |
| Soluble starch | 5.0 mg |
| Magnesium stearate | 3.0 mg |
| Total | 200.0 mg |

Procedure

The active ingredient was mixed with some of the excipients and granulated with a solution of the soluble starch in water. After the granulate was dried, the remaining excipients were added and the mixture was compressed to form tablets.

EXAMPLE 81

Coated Tablets
Composition of one coated tablet:

| Component | Amount |
|---|---|
| Active ingredient according to the invention | 20.0 mg |
| Lactose | 100.0 mg |
| Corn starch | 65.0 mg |
| Colloidal silicic acid | 2.0 mg |
| Soluble starch | 5.0 mg |
| Magnesium stearate | 3.0 mg |
| Total | 195.0 mg |

Procedure

The active ingredient and excipients were compressed to form tablet cores as described in Example 80, and these cores were then coated in the usual way with sugar, talc, and gum arabic.

EXAMPLE 82

Suppositories
Composition of one suppository:

| Component | Amount |
|---|---|
| Active ingredient according to the invention | 50.0 mg |
| Lactose | 250.0 mg |

| Suppositories Composition of one suppository: | |
|---|---|
| Component | Amount |
| Suppository composition q.s.ad | 1.7 gm |

Procedure

The active substance and lactose were mixed together, and the mixture was homogeneously suspended in the molten suppository composition. The suspensions were poured into cooled molds to form suppositories weighing 1.7 gm apiece.

EXAMPLE 83

| Ampules Composition of one ampule: | |
|---|---|
| Component | Amount |
| Active ingredient according to the invention | 20.0 mg |
| Sodium chloride | 5.0 mg |
| Twice distilled water q.s.ad | 2.0 ml |

Procedure

The active substance and sodium chloride were dissolved in water which had been distilled twice, and the solution was transferred into ampules under sterile conditions.

EXAMPLE 84

| Ampules Composition of one ampule: | |
|---|---|
| Component | Amount |
| Active ingredient according to the invention | 10.0 mg |
| Sodium chloride | 7.0 mg |
| Twice distilled water q.s.ad | 1.0 ml |

The procedure was analogous to that of Example 83.

EXAMPLE 85

| Drops Composition of one vial: | |
|---|---|
| Component | Amount |
| Active ingredient according to the invention | 0.70 gm |
| Methyl p-hydroxybenzoate | 0.07 gm |
| Propyl p-hydroxybenzoate | 0.03 gm |
| Demineralized water q.s.ad | 100.00 ml |

Procedure

The active ingredient and preservatives were dissolved in demineralized water, and the resulting solution was filtered and transferred into vials each containing 100 ml.

Any one of the other compounds embraced by Formula I or a non-toxic, pharmacologically acceptable salt thereof with an inorganic or organic acid, may be substituted for the particular active ingredient employed in Examples 80 through 85. Likewise, the amount of active ingredient in these illustrative examples may be varied to achieve the dosage unit range set forth above, and the amounts and nature of the inert pharmaceutical carrier ingredient may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

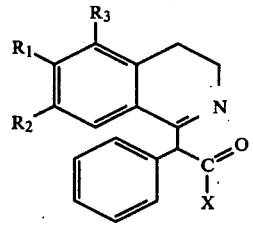

wherein
$R_1$, $R_2$, $R_3$, which may be the same or different, each represent a hydrogen, hydroxyl, or methoxy group or $R_1$ and $R_2$, $R_2$ and $R_3$, or $R_1$ and $R_3$ together represents a methylenedioxy group; and X represents a dialkylamino in which each alkyl moiety has from 1 to 3 carbon atoms; a heterocyclic group; or the group

—NHR wherein R represents a lower alkyl group of from 1 to 4 carbon atoms; alkenyl or alkinyl group of 3 carbon atoms; cycloalkyl group of from 3 to 6 carbon atoms; morpholino group; pyridyl group; or ethyl or propyl group substituted by a hydroxyl, methoxy, dimethylamino, phenyl, methoxyphenyl, dimethoxyphenyl, methylenedioxyphenyl, morpholino, or indolyl group, in racemic or optically active form, or a non-toxic, pharmacologically acceptable acid addition salt thereof.

2. A compound of claim 1, wherein
$R_1$, $R_2$, and $R_3$ each represent a hydrogen or methoxy, or $R_1$ and $R_2$, $R_2$ and $R_3$, or $R_1$ and $R_3$ represent a methylenedioxy group, and X represents a dialkylamino in which each alkyl moiety has from 1 to 3 carbon atoms or a heterocyclic group, in racemic or optically active form, or a non-toxic, pharmacologically acceptable acid addition salt thereof.

3. A compound of claims 1 or 2, wherein X is a heterocyclic group selected from the group consisting of aziridinyl, azetidinyl, pyrrolidinyl, morpholino, N'-methylpiperazino, and N'-benzylpiperazino groups.

4. The compound of claim 1 which comprises 1-(α-diethylaminocarbonyl-benzyl)-6,7-dimethoxy-3,4-dihydroisoquinoline in the optically active or racemic form or a pharmacologically acceptable acid addition salt thereof.

5. The compound of claim 1 which comprises α-hydroxyethylaminocarbonyl-1-benzyl-6,7-dimethoxy-3,4-dihydroxyisoquinoline hydrochloride in the optically active or racemic form or a pharmacologically acceptable acid addition salt thereof.

6. A pharmaceutical dosage unit composition consisting essentially of an inert pharmaceutical carrier and an effective amount of a composition of claim 1.

7. A method of promoting blood flow and stimulating the circulation in a warm-blooded animal which comprises perorally, parenterally, or rectally administering to said animal an effective blood circulation stimulating amount of a compound of claim 1.

* * * * *

UNITED STATES PATENT AND TRADEMARK OFFICE
CERTIFICATE OF CORRECTION

PATENT NO. : 4,322,418
DATED : March 30, 1982
INVENTOR(S) : WALTER LÖSEL ET AL.

It is certified that error appears in the above—identified patent and that said Letters Patent is hereby corrected as shown below:

Column 4, line 4: "dimethoxyphenyl-ethylamide" should read -- dimethoxyphenyl)-ethylamide --.

Column 4, line 25: "ethyla-" should reach -- ethyl- --.

Column 4, line 26: "mide" should read -- amide --.

Column 7, last line (Example 54): "154-" should read -- 154-158° --.

Column 8, line 45 (Example 54): Delete "158°".

Column 12, line 55: "heter-" should read -- hetero- --.

Column 12, line 56: "ocyclic" should read -- cyclic --.

Signed and Sealed this

Thirteenth Day of July 1982

[SEAL]

Attest:

*Attesting Officer*

GERALD J. MOSSINGHOFF
*Commissioner of Patents and Trademarks*